(12) United States Patent
Djupesland et al.

(10) Patent No.: US 11,690,969 B2
(45) Date of Patent: Jul. 4, 2023

(54) DELIVERY OF GASES TO THE NASAL AIRWAY

(71) Applicant: OptiNose AS, Oslo (NO)

(72) Inventors: Per Gisle Djupesland, Oslo (NO); Roderick Peter Hafner, Wiltshire (GB)

(73) Assignee: OptiNose Inc., Yardley, PA (US)

( * ) Notice: Subject to any disclaimer, the term of this patent is extended or adjusted under 35 U.S.C. 154(b) by 326 days.

(21) Appl. No.: 16/986,692

(22) Filed: Aug. 6, 2020

(65) Prior Publication Data

US 2021/0085907 A1 Mar. 25, 2021

Related U.S. Application Data

(63) Continuation of application No. 15/869,284, filed on Jan. 12, 2018, now Pat. No. 10,765,829, which is a (Continued)

(30) Foreign Application Priority Data

Jul. 25, 2006 (GB) ..................... 0614811

(51) Int. Cl.
*A61M 16/00* (2006.01)
*A61M 16/06* (2006.01)
(Continued)

(52) U.S. Cl.
CPC .... *A61M 16/0672* (2014.02); *A61M 15/0003* (2014.02); *A61M 15/0028* (2013.01); *A61M 15/0065* (2013.01); *A61M 15/0098* (2014.02); *A61M 15/08* (2013.01); *A61M 16/0003* (2014.02); *A61M 16/0057* (2013.01); *A61M 16/101* (2014.02); *A61M 16/122* (2014.02); *A61M 16/142* (2014.02);
(Continued)

(58) Field of Classification Search
CPC .......... A61M 16/0672; A61M 15/0003; A61M 15/0098; A61M 16/0003; A61M 16/101; A61M 16/122; A61M 16/142; A61M 15/0028; A61M 15/0065; A61M 15/08; A61M 16/0057; A61M 16/22; A61M 15/025; A61M 16/0808; A61M 2016/0021
See application file for complete search history.

(56) References Cited

U.S. PATENT DOCUMENTS 605,436 A 6/1898 Kellogg
642,748 A 2/1900 Manners
(Continued)

FOREIGN PATENT DOCUMENTS

GB 2 404 867 2/2005
GB 2418 147 3/2006
(Continued)

OTHER PUBLICATIONS

Cindy H. Dubin, *Nothing to Sneeze At*, Pharmaceutical Formulation & Quality Magazine (Jan. 29, 2003).
(Continued)

*Primary Examiner* — Steven O Douglas
(74) *Attorney, Agent, or Firm* — Finnegan, Henderson, Farabow, Garrett & Dunner, LLP

(57) ABSTRACT

A delivery device for and a method of delivering gases to the nasal airway, in particular therapeutic gases and gases in combination with active substances, either as powders or liquids, for enhanced uptake of the active substances.

22 Claims, 5 Drawing Sheets

Related U.S. Application Data continuation of application No. 14/560,053, filed on Dec. 4, 2014, now abandoned, which is a continuation of application No. 12/375,115, filed as application No. PCT/GB2007/002829 on Jul. 25, 2007, now Pat. No. 8,910,629.

(51) Int. Cl.

| | |
|---|---|
| *A61M 15/00* | (2006.01) |
| *A61M 16/14* | (2006.01) |
| *A61M 15/08* | (2006.01) |
| *A61M 16/10* | (2006.01) |
| *A61M 16/12* | (2006.01) |
| *A61M 16/22* | (2006.01) |
| *A61M 15/02* | (2006.01) |
| *A61M 16/08* | (2006.01) |

(52) U.S. Cl.
CPC .......... *A61M 16/22* (2013.01); *A61M 15/025* (2014.02); *A61M 16/0808* (2013.01); *A61M 2016/003* (2013.01); *A61M 2016/0021* (2013.01); *A61M 2016/0027* (2013.01); *A61M 2016/0042* (2013.01); *A61M 2202/025* (2013.01); *A61M 2202/0208* (2013.01); *A61M 2202/0225* (2013.01); *A61M 2202/0266* (2013.01); *A61M 2202/0275* (2013.01); *A61M 2202/064* (2013.01); *A61M 2205/3334* (2013.01); *A61M 2210/0625* (2013.01)

(56) References Cited

U.S. PATENT DOCUMENTS

| | | | |
|---|---|---|---|
| 658,436 | A | 9/1900 | Groth |
| 746,749 | A | 12/1903 | Seidel |
| 794,641 | A | 7/1905 | Ramey |
| 902,832 | A | 11/1908 | Philbrook |
| 2,470,297 | A | 5/1949 | Fields |
| 5,797,392 | A | 8/1998 | Keldmann et al. |
| 5,850,833 | A | 12/1998 | Kotliar |
| 6,581,592 | B1 | 6/2003 | Bathe et al. |
| 6,648,848 | B1 | 11/2003 | Keldmann et al. |
| 6,715,485 | B1 | 4/2004 | Djupesland |
| D530,815 | S | 10/2006 | Murphy et al. |
| 7,347,201 | B2 | 3/2008 | Djupesland |
| 7,377,901 | B2 | 5/2008 | Djupesland et al. |
| 7,481,218 | B2 | 1/2009 | Djupesland |
| 7,543,581 | B2 | 6/2009 | Djupesland |
| 7,740,014 | B2 | 6/2010 | Djupesland |
| 7,784,460 | B2 | 8/2010 | Djupesland et al. |
| 7,841,337 | B2 | 11/2010 | Djupesland |
| 7,854,227 | B2 | 12/2010 | Djupesland |
| 7,934,503 | B2 | 5/2011 | Djupesland et al. |
| 7,975,690 | B2 | 7/2011 | Djupesland |
| 8,047,202 | B2 | 11/2011 | Djupesland |
| 8,146,589 | B2 | 4/2012 | Djupesland |
| 8,171,929 | B2 | 5/2012 | Djupesland et al. |
| 8,327,844 | B2 | 12/2012 | Djupesland |
| 8,511,303 | B2 | 8/2013 | Djupesland |
| 8,522,778 | B2 | 9/2013 | Djupesland |
| 8,550,073 | B2 | 10/2013 | Djupesland |
| 8,555,877 | B2 | 10/2013 | Djupesland |
| 8,555,878 | B2 | 10/2013 | Djupesland |
| 8,590,530 | B2 | 11/2013 | Djupesland et al. |
| 8,596,278 | B2 | 12/2013 | Djupesland |
| 8,800,555 | B2 | 8/2014 | Djupesland |
| 8,875,704 | B2 | 11/2014 | Djupesland et al. |
| 8,899,229 | B2 | 12/2014 | Djupesland et al. |
| 8,910,629 | B2 | 12/2014 | Djupesland et al. |
| D723,156 | S | 2/2015 | Djupesland et al. |
| D725,769 | S | 3/2015 | Djupesland et al. |
| 8,978,647 | B2 | 3/2015 | Djupesland et al. |
| 9,010,325 | B2 | 4/2015 | Djupesland et al. |
| 9,038,630 | B2 | 5/2015 | Djupesland et al. |
| 9,067,034 | B2 | 6/2015 | Djupesland et al. |
| 9,072,857 | B2 | 7/2015 | Djupesland |
| 9,108,015 | B2 | 8/2015 | Djupesland |
| 9,119,932 | B2 | 9/2015 | Djupesland |
| 9,132,249 | B2 | 9/2015 | Djupesland |
| 9,144,652 | B2 | 9/2015 | Djupesland et al. |
| 9,168,341 | B2 | 10/2015 | Djupesland |
| 9,205,208 | B2 | 12/2015 | Djupesland |
| 9,205,209 | B2 | 12/2015 | Djupesland |
| 9,272,104 | B2 | 3/2016 | Djupesland |
| D759,805 | S | 6/2016 | Djupesland |
| D761,951 | S | 7/2016 | Djupesland |
| 9,452,272 | B2 | 9/2016 | Djupesland et al. |
| 9,468,727 | B2 | 10/2016 | Djupesland |
| D773,644 | S | 12/2016 | Djupesland |
| 9,522,243 | B2 | 12/2016 | Djupesland |
| 9,566,402 | B2 | 2/2017 | Djupesland |
| 9,649,456 | B2 | 5/2017 | Djupesland et al. |
| D809,128 | S | 1/2018 | Djupesland |
| 2004/0024330 | A1 | 2/2004 | Djupesland et al. |
| 2004/0112378 | A1 | 6/2004 | Djupesland |
| 2004/0112379 | A1 | 6/2004 | Djupesland |
| 2004/0112380 | A1 | 6/2004 | Djupesland |
| 2004/0149289 | A1 | 8/2004 | Djupesland |
| 2004/0182388 | A1 | 9/2004 | Djupesland |
| 2005/0028812 | A1 | 2/2005 | Djupesland |
| 2005/0072430 | A1 | 4/2005 | Djupesland |
| 2005/0235992 | A1 | 10/2005 | Djupesland |
| 2006/0096589 | A1 | 5/2006 | Djupesland |
| 2006/0107957 | A1 | 5/2006 | Djupesland |
| 2006/0169278 | A1 | 8/2006 | Djupesland et al. |
| 2006/0219240 | A1 | 10/2006 | Djupesland |
| 2006/0219241 | A1 | 10/2006 | Djupesland |
| 2006/0225732 | A1 | 10/2006 | Djupesland |
| 2006/0231094 | A1 | 10/2006 | Djupesland |
| 2007/0039614 | A1 | 2/2007 | Djupesland |
| 2007/0125371 | A1 | 6/2007 | Djupesland |
| 2007/0186927 | A1 | 8/2007 | Djupesland et al. |
| 2008/0161771 | A1 | 7/2008 | Djupesland |
| 2008/0163874 | A1 | 7/2008 | Djupesland |
| 2008/0221471 | A1 | 9/2008 | Djupesland et al. |
| 2008/0223363 | A1 | 9/2008 | Djupesland |
| 2008/0289629 | A1 | 11/2008 | Djupesland et al. |
| 2009/0101146 | A1 | 4/2009 | Djupesland |
| 2009/0293873 | A1 | 12/2009 | Djupesland et al. |
| 2009/0304802 | A1 | 12/2009 | Djupesland et al. |
| 2009/0314293 | A1 | 12/2009 | Djupesland |
| 2009/0320832 | A1 | 12/2009 | Djupesland |
| 2010/0035805 | A1 | 2/2010 | Hafner |
| 2010/0051022 | A1 | 3/2010 | Djupesland et al. |
| 2010/0057047 | A1 | 3/2010 | Djupesland et al. |
| 2010/0199984 | A1 | 8/2010 | Williams et al. |
| 2010/0242959 | A1 | 9/2010 | Djupesland et al. |
| 2010/0282246 | A1 | 11/2010 | Djupesland et al. |
| 2010/0288275 | A1 | 11/2010 | Djupesland et al. |
| 2010/0300439 | A1 | 12/2010 | Djupesland et al. |
| 2011/0023869 | A1 | 2/2011 | Djupesland |
| 2011/0053827 | A1 | 3/2011 | Hafner |
| 2011/0088690 | A1 | 4/2011 | Djupesland et al. |
| 2011/0088691 | A1 | 4/2011 | Djupesland |
| 2011/0114087 | A1 | 5/2011 | Djupesland et al. |
| 2011/0120456 | A1 | 5/2011 | Immel |
| 2011/0126830 | A1 | 6/2011 | Djupesland et al. |
| 2011/0259329 | A1 | 10/2011 | Djupesland et al. |
| 2011/0318345 | A1 | 12/2011 | Djupesland |
| 2012/0000459 | A1 | 1/2012 | Djupesland |
| 2012/0006323 | A1 | 1/2012 | Djupesland |
| 2012/0073571 | A1 | 3/2012 | Djupesland |
| 2012/0090608 | A1 | 4/2012 | Djupesland et al. |
| 2012/0260915 | A1 | 10/2012 | Djupesland |
| 2013/0098362 | A1 | 4/2013 | Djupesland et al. |
| 2013/0125889 | A1 | 5/2013 | Djupesland et al. |
| 2013/0327320 | A1 | 12/2013 | Djupesland |
| 2014/0018295 | A1 | 1/2014 | Djupesland |
| 2014/0041660 | A1 | 2/2014 | Djupesland et al. |
| 2014/0060536 | A1 | 3/2014 | Djupesland |
| 2014/0073562 | A1 | 3/2014 | Djupesland |
| 2014/0144442 | A1 | 5/2014 | Djupesland et al. |

(56) References Cited

U.S. PATENT DOCUMENTS

| | | |
|---|---|---|
| 2014/0144443 A1 | 5/2014 | Djupesland et al. |
| 2014/0166008 A1 | 6/2014 | Djupesland |
| 2014/0202456 A1 | 7/2014 | Djupesland |
| 2014/0246022 A1 | 9/2014 | Djupesland et al. |
| 2015/0007811 A1 | 1/2015 | Djupesland et al. |
| 2015/0013670 A1 | 1/2015 | Djupesland et al. |
| 2015/0013677 A1 | 1/2015 | Djupesland et al. |
| 2015/0053201 A1 | 2/2015 | Djupesland et al. |
| 2015/0090259 A1 | 4/2015 | Djupesland et al. |
| 2015/0101605 A1 | 4/2015 | Djupesland et al. |
| 2015/0144129 A1 | 5/2015 | Djupesland et al. |
| 2015/0165139 A1 | 6/2015 | Hafner |
| 2015/0182709 A1 | 7/2015 | Djupesland |
| 2015/0246194 A1 | 9/2015 | Djupesland et al. |
| 2015/0367090 A1 | 12/2015 | Djupesland et al. |
| 2015/0367091 A1 | 12/2015 | Djupesland et al. |
| 2016/0001022 A1 | 1/2016 | Djupesland et al. |
| 2016/0045687 A1 | 2/2016 | Djupesland |
| 2016/0051778 A1 | 2/2016 | Djupesland et al. |
| 2016/0074603 A1 | 3/2016 | Djupesland et al. |
| 2016/0082206 A1 | 3/2016 | Djupesland et al. |
| 2016/0082207 A1 | 3/2016 | Djupesland et al. |
| 2016/0095989 A1 | 4/2016 | Djupesland |
| 2016/0095993 A1 | 4/2016 | Djupesland |
| 2016/0101249 A1 | 4/2016 | Djupesland |
| 2016/0166788 A1 | 6/2016 | Djupesland et al. |
| 2016/0184537 A1 | 6/2016 | Djupesland |
| 2016/0193435 A1 | 7/2016 | Djupesland |
| 2016/0250408 A1 | 9/2016 | Djupesland |
| 2016/0263334 A1 | 9/2016 | Djupesland |
| 2016/0279357 A1 | 9/2016 | Djupesland |
| 2016/0310683 A1 | 10/2016 | Djupesland et al. |
| 2016/0331916 A1 | 11/2016 | Djupesland et al. |
| 2016/0367771 A1 | 12/2016 | Djupesland |
| 2016/0367772 A1 | 12/2016 | Djupesland |
| 2016/0367774 A1 | 12/2016 | Djupesland et al. |
| 2017/0043108 A1 | 2/2017 | Djupesland et al. |
| 2017/0151397 A1 | 6/2017 | Djupesland |
| 2017/0203061 A1 | 7/2017 | Djupesland et al. |
| 2017/0216540 A1 | 8/2017 | Djupesland |
| 2017/0274164 A1 | 9/2017 | Djupesland et al. |
| 2017/0333649 A1 | 11/2017 | Djupesland |

FOREIGN PATENT DOCUMENTS

| | | |
|---|---|---|
| WO | WO 96/22802 | 8/1996 |
| WO | WO 98/53869 | 12/1998 |
| WO | WO 00/51672 | 9/2000 |
| WO | WO 01/03645 | 1/2001 |
| WO | WO 01/97689 | 12/2001 |
| WO | WO 02/068029 | 9/2002 |
| WO | WO 02/068030 | 9/2002 |
| WO | WO 02/068031 | 9/2002 |
| WO | WO 02/068032 | 9/2002 |
| WO | WO 03/000310 | 1/2003 |
| WO | WO 03/020350 | 3/2003 |
| WO | WO 03/045483 | 6/2003 |
| WO | WO 03/082393 | 10/2003 |
| WO | WO 03/084591 | 10/2003 |
| WO | WO 03/090812 | 11/2003 |
| WO | WO 03/094694 | 11/2003 |
| WO | WO 2004/004814 | 1/2004 |
| WO | WO 2004/004922 | 1/2004 |
| WO | WO 2004/060433 | 7/2004 |
| WO | WO 2004/103447 | 12/2004 |
| WO | WO 2005/007056 | 1/2005 |
| WO | WO 2005/016423 | 2/2005 |
| WO | WO 2005/021059 | 3/2005 |
| WO | WO 2006/030210 | 3/2006 |
| WO | WO 2006/090149 | 8/2006 |
| WO | WO 2007/083073 | 7/2007 |
| WO | WO 2007/093784 | 8/2007 |
| WO | WO 2007/093791 | 8/2007 |
| WO | WO 2007/099361 | 9/2007 |
| WO | WO 2007/102089 | 9/2007 |
| WO | WO 2007/107887 | 9/2007 |
| WO | WO 2007/125318 | 11/2007 |
| WO | WO 2007/141541 | 12/2007 |
| WO | WO 2008/012531 | 1/2008 |
| WO | WO 2008/065403 | 6/2008 |
| WO | WO 2008/081326 | 7/2008 |
| WO | WO 2008/081327 | 7/2008 |
| WO | WO 2008/122791 | 10/2008 |
| WO | WO 2008/122795 | 10/2008 |
| WO | WO 2009/044172 | 4/2009 |
| WO | WO 2010/029441 | 3/2010 |
| WO | WO 2012/035427 | 3/2012 |
| WO | WO 2012/123819 | 9/2012 |
| WO | WO 2013/124491 | 8/2013 |
| WO | WO 2013/124492 | 8/2013 |
| WO | WO 2013/124493 | 8/2013 |
| WO | WO 2014/155192 | 10/2014 |

OTHER PUBLICATIONS

Per Gisle Djupesland, *Nasal Delivery of Vaccines*, EPC (Jan. 29, 2003).

Per Gisle Djupesland, *Who Nose How Far Nasal Delivery Can Go?*, EPC (Oct. 7, 2003).

Per Gisle Djupesland, *Bi-directional Nasal Drug Delivery*, Innovations in Pharmaceutical Technology (Jul. 10, 2004).

P.G. Djupesland, *Bi-Directional Nasal Delivery of Aerosols Can Prevent Lung Deposition*, Journal of Aerosol Medicine (Sep. 2004).

*Bi-Directional Nasal Device Delivers Drug on Exhalation*, Pharmaceutical Technology (Sep. 10, 2004).

Ola Dale et al., *Intranasal Midazolam: A Comparison of Two Delivery Devices in Human Volunteers*, Journal of Pharmacy and Pharmacology (Oct. 2004).

G. Furness, *Nasal Drug Delivery: Rapid Onset Via A Convenient Route*, ONdrugDelivery Ltd. (2005).

M. Kleven, *Using Computational Fluid Dynamics (CFD) to Improve the Bi-Directional Nasal Drug Delivery Concept*, Trans IChemE Part C. (Jun. 2005).

Per Gisle Djupesland, *Breath-Actuated Bi-Directional Delivery Sets the Nasal Market on a New Course*, ONdrugDelivery (Oct. 10, 2005).

Hilde Bakke et al., *Oral Spray Immunization May be An Alternative to Intranasal Vaccine Delivery to Induce Systemic Antibodies But Not Nasal Mucosal or Cellular Immunity*, Scan J. of Immunol. (Mar. 2006).

P.G. Djupesland et al., *Breath Actuated Nasal Device Improves Delivery to Target Sites Beyond the Nasal Valve*, The Laryngoscope (Mar. 2006).

R. Luthringer et al., *Rapid Absorption of Sumatriptan Powder and Effects on Glyceryl tinitrate Model of Headache Following Intranasal Delivery Using A Novel Bi-Directional Device*, Journal of Pharmacy and Pharmacology (Jan. 2009).

A. Skretting et al., *A New Method for Scintigraphic Quantification of Deposition and Clearance in Anatomical Regions of the Human Nose*, Nuclear Medicine Communications (Aug. 2009).

Vlckovia et al., *Effective Treatment Of Mild-to-Moderate Nasal Polyposis with Fluticasone Delivered By A Novel Device*, Rhinology (Oct. 22, 2009).

Per Gisle Djupesland et al., *Impact of Baseline Nasal Polyp Size and Previous Surgery on Efficacy of Fluticasone Delivered With a Novel Device: A Subgroup Analysis*, Am. J. Rhinology Allergy (2010).

P.G. Djupesland et al., *Intranasal Sumatriptan Powder Delivered by a Novel Breath Actuated Bi-Directional Device for the Acute Treatment of Migraine: A Randomised Placebo-Controlled Study*, Cephalalgia (Mar. 17, 2010).

F.S. Hansen et al., *Preliminary Efficacy of Fluticasone Delivered By a Novel Device in Recalcitrant Chronic Rhinosinusitis*, Rhinology (Jun. 26, 2010).

Per Gisle Djupesland, *Nasal Drug Delivery Devices: Characteristics and Performance in Clinical Perspective—A Review*, Drug. Deliv. and Transl. Res. (Oct. 18, 2012).

Per Gisle Djupesland, *Nasal Deposition and Clearance in Man: Comparison of a Bidirectional Powder Device and a Traditional Liquid Spray Pump*, Journal of Aerosol Medicine and Pulmonary Drug Delivery (Nov. 2012).

(56) References Cited

OTHER PUBLICATIONS

Stewart J. Tepper, *Clinical Implications for Breath-Powered Powder Sumatriptan Intranasal Treatment*, Headache, The American Headache Society (Apr. 29, 2013).
Mohammad Obaidi et al., *Improved Pharmacokinetics of Sumatriptan With Breath Powered Nasal Delivery of Sumatriptan Powder*, Headache, The American Headache Society (May 24, 2013).
Per Gisle Djupesland, *Breath Powdered Nasal Delivery: A New Route to Rapid Headache Relief*, Headache, The American Headache Society (Jun. 4, 2013).
Per Gisle Djupesland et al., *The Nasal Approach to Delivering Treatment for Brain Diseases: An Anatomic, Physiologic, and Delivery Technology Overview*, Therapeutic Delivery (2014).
R.K. Cady et al., *A Randomized Double-Blind, Placebo Controlled Study of Breath Powered Nasal Delivery of Sumatriptan Powder (AVP-825) in the Treatment of Acute Migraine (The TARGET Study)*, Headache (Sep. 8, 2014).
S.J. Tepper et al., *AVP-825 Breath-Powdered Intranasal Delivery System Containing 22 mg Sumatriptan Powder vs. 100 mg Oral Sumatripta in the Acute Treatment of Migraines (The COMPASS Study): A Comparative Randomized Clinical Trial Across Multiple Attacks*, Headache: The Journal of Head and Face Pain (Mar. 29, 2015).
D. S. Quintana et al., *Low-dose Oxytocin Delivered Intranasally with Breath Powdered Device Affects Social-Cognitive Behavior: A Randomized Four-Way Crossover Trial with Nasal Cavity Dimension Assessment*, Transl Psychiatry (Jul. 14, 2015).
R. Mahmoud, *Breathe Out*, Innovations in Phar, Tech. (Dec. 10, 2015).

DELIVERY OF GASES TO THE NASAL AIRWAY

This application is a Continuation of U.S. application Ser. No. 15/869,284, filed Jan. 12, 2018, which is a Continuation of U.S. application Ser. No. 14/560,053, filed Dec. 4, 2014, now abandoned, which is a Continuation of U.S. patent application Ser. No. 12/375,115, filed on Apr. 23, 2010, now U.S. Pat. No. 8,910,629, which is a U.S. National phase application of PCT/GB2007/002829 filed Jul. 25, 2007, which claims priority to GB 0614811.8, filed Jul. 25, 2006, the disclosure of which applications are incorporated herein by reference.

FIELD OF INVENTION

The present invention relates to a device for and a method of delivering gases to the nasal airway, in particular therapeutic gases and gases in combination with active substances, either as powders or liquids, for enhanced uptake of the active substances.

BACKGROUND

The delivery of gases, in particular carbon dioxide, nitric oxide, oxygen and helium, to the nasal airway for therapeutic application is known, as disclosed, for example, in WO-A-2001/003645.

Gas therapy for the treatment of headaches, allergies, asthma, and other conditions as well as associated physiology is described in the following references in the medical literature:

Carbon Dioxide Therapy
Diamond S, Migraine headache—its diagnosis and treatment. 13$^{th}$ Annual Practicing Physician's Approach to the Difficult Headache Patient,
Rancho Mirage, C A, Feb. 5-19, 2000
Fisher H K et al, *Am Rev Respir Dis* 114(5):861, 1976
Fisher H K et al, *Am Rev Respir Dis* 101:855-896, 1970
Gillman M A et al, *Br J Psychiatry* 159:672-5, 1991
Grosshans V A et al, *Z Gesamte Inn Med* 42(23):667-70, 1987
Harrowes W M C et al, Fractional administration of carbon dioxide in the treatment of neuroses, *Carbon Dioxide Therapy A Neurophysiological Treatment of Nervous Disorders*. Second Edition. L J Meduna Editor, Charles C Thomas Publisher, Springfield, Ill. 1958
Jozefowicz R F, *Neurologic Manifestations of Systemic Disease* 7(3):605-616, 1989
La Verne A A, *Dis Nerv System* 14:5, 1953
Leake C D et al, *Calif West Med* 31:20, 1929
Loevenhart A S et al, *JAMA* 92(11), 1929
MacRae D, Carbon dioxide in paediatrics, *Carbon Dioxide Therapy A Neurophysiological Treatment of Nervous Disorders*. Second Edition. L J Meduna Editor, Charles C Thomas publisher, Springfield, Ill., 1958
Marcussen R M et al, *Arch Neurol Psychiatry* 63:42-51, 1950
Meduna L J, *Dis Nerv System* 8(2), 1947
Meduna L J, *J Nerv & Ment Dis* 108:373, 1948
Meduna L J Ed, *Carbon Dioxide Therapy A Neurophysiological Treatment of Nervous Disorders*. Second Edition. Charles C Thomas Publisher, Springfield, Ill. 1958
Moriarty J D, Prognosis with carbon dioxide therapy, including the epinephrine-mecholyl test (Funkenstein test), *Carbon Dioxide Therapy A Neurophysiological Treatment of Nervous Disorders*. Second Edition. L J Meduna Editor, Charles C Thomas Publisher, Springfield, Ill., 1958
Moriarty J D, *J Clin & Exper Psychopath* 13(3), 1952
National Headache Foundation. A patients guide to migraine prevention & treatment, Chicago, Ill., August 1996.
Rodarte J R et al, *Resp Physiol* 17:135-145, 1973
Singh V et al, *Lancet* 335:1381-3, 1990
Wilkinson W E, Some clinical observations pertaining to the effects of carbon dioxide on the biology of mental disease, *Carbon Dioxide Therapy A Neurophysiological Treatment of Nervous Disorders*. Second Edition. L J Meduna Editor, Charles C Thomas Publisher, Springfield, Ill., 1958
Wilmoth D F et al, *AACN Clin Issues* 7(4):473-81, 1996

Nitric Oxide Therapy
Pagano D et al, *Eur J Cardiothorac Surg* 10(12):1120-6, 1996
Ream R S et al, *Crit Care Med* 27(5):989-96, 1999
Schenk P et al, *Ann Emerg Med* 33(6):710-4, 1999

Helium Therapy
Hollman G et al, *Crit Care Med* 26(10):1731-6, 1998
Jolliet P et al, *Crit Care Med* 27(11):2422-9, 1999
Schaeffer E M et al, *Crit Care Med* 27(12):2666-70, 1999

Such gases have been shown to have a local effect on topical diseases which affect the nasal mucosa, such as rhinitis, sinusitis, polyposis and allergies, and also on nerves and ganglia in relieving or treating pain conditions, such as peripheral and local neuralgia, for example, trigeminal neuralgia.

Such gases can also have effect in relieving or treating both local and central pain conditions or other neurological pathologies, such as migraine and other primary or secondary headache conditions.

SUMMARY OF THE INVENTION

As noted in WO-A-2001/003645, the delivery of therapeutic gases to the nasal airway is problematic, insofar as delivery of the gases to the nasal airway leads to inhalation of the gases.

The present inventors have also recognized that the amount of a therapeutic gas as conventionally delivered to the nasal airway cannot be controlled.

It is one aim of the present invention to provide a device for and method of delivering gases to the nasal airway, in particular therapeutic gases, which avoids the possibility of inhalation and allows for delivery of the gases at significantly higher concentrations.

It is another aim of the present invention to provide an improved device and method for delivering gases to the nasal airway, in particular therapeutic gases and gases in combination with active substances, either as powders or liquids, for enhanced uptake of the active substances.

In one aspect the present invention provides a delivery device for providing a therapeutic gas to the nasal airway of a subject, the delivery device comprising: a nosepiece for fitting to one nostril of the subject; a mouthpiece through which the subject in use exhales and which is fluidly connected to the nosepiece; and a scrubber which is operative at least to reduce the concentration of at least one gas from an exhaled breath of the subject as delivered through the mouthpiece and provide a gas flow to the nosepiece which has an increased concentration of at least one other, therapeutic gas which provides a therapeutic effect.

In one embodiment the scrubber is operative to reduce the concentration of at least two gases from an exhaled breath of the subject.

In one embodiment the at least one gas comprises nitrogen.

In one embodiment the at least one gas comprises oxygen.

In one embodiment the at least one other, therapeutic gas comprises oxygen.

In one embodiment the at least one gas comprises carbon dioxide.

In one embodiment the at least one other, therapeutic gas comprises carbon dioxide.

Preferably, the scrubber is operative to provide a gas flow which has a concentration of the at least one other, therapeutic gas of at least 10 vol %.

More preferably, the scrubber is operative to provide a gas flow which has a concentration of the at least one other, therapeutic gas of at least 15 vol %.

Still more preferably, the scrubber is operative to provide a gas flow which has a concentration of the at least one other, therapeutic gas of at least 20 vol %.

Yet more preferably, the scrubber is operative to provide a gas flow which has a concentration of the at least one other, therapeutic gas of at least 30 vol %.

Yet still more preferably, the scrubber is operative to provide a gas flow which has a concentration of the at least one other, therapeutic gas of at least 40 vol %.

Still yet more preferably, the scrubber is operative to provide a gas flow which has a concentration of the at least one other, therapeutic gas of at least 50 vol %.

In one embodiment the delivery device further comprises: a further nosepiece for fitting to the other nostril of the subject; and a pressure regulator which is fluidly connected to the other nosepiece, such as to provide for control of a pressure regime within the nasal airway of the subject.

In another aspect the present invention provides a delivery device for providing a therapeutic gas to the nasal airway of a subject, the delivery device comprising: a nosepiece for fitting to one nostril of the subject; and a therapeutic gas supply unit for supplying at least one therapeutic gas to the nosepiece, such as to provide for delivery of the at least one therapeutic gas to the nasal airway of the subject.

In one embodiment the at least one therapeutic gas comprises carbon dioxide.

In one embodiment the at least one therapeutic gas comprises nitric oxide.

In one embodiment the at least one therapeutic gas comprises oxygen.

In one embodiment the at least one therapeutic gas comprises helium.

In one embodiment the delivery device further comprises: a mouthpiece through which the subject in use exhales.

In one embodiment the mouthpiece is fluidly connected to the nosepiece, such that a gas flow as developed from an exhalation breath of the subject is delivered through the nosepiece.

In another embodiment the mouthpiece is fluidly separated from the nosepiece, such that a gas flow as developed from an exhalation breath of the subject is not delivered through the nosepiece.

In one embodiment the therapeutic gas supply unit comprises a therapeutic gas generator which is operative to generate at least one therapeutic gas.

In one embodiment the therapeutic gas generator is operative to generate at least one therapeutic gas on exhalation by the subject through the mouthpiece.

In one embodiment the therapeutic gas generator comprises a therapeutic gas generating agent which reacts to generate the at least one therapeutic gas.

In one embodiment the therapeutic gas generator comprises a therapeutic gas generating agent which is reactive to moisture in the exhalation breath of the subject.

In another embodiment the therapeutic gas supply unit comprises a gas supply which is actuatable to deliver at least one therapeutic gas.

In one embodiment the therapeutic gas supply unit comprises a breath-actuated release mechanism which actuates the gas supply to deliver at least one therapeutic gas in response to exhalation by the subject through the mouthpiece.

Preferably, the gas supply unit provides a gas flow which has a concentration of the at least one therapeutic gas of at least 10 vol %.

More preferably, the gas supply unit provides a gas flow which has a concentration of the at least one therapeutic gas of at least 15 vol %.

Still more preferably, the gas supply unit provides a gas flow which has a concentration of the at least one therapeutic gas of at least 20 vol %.

Yet more preferably, the gas supply unit provides a gas flow which has a concentration of the at least one therapeutic gas of at least 30 vol %.

Still yet more preferably, the gas supply unit provides a gas flow which has a concentration of the at least one therapeutic gas of at least 40 vol %.

Yet still more preferably, the gas supply unit provides a gas flow which has a concentration of the at least one therapeutic gas of at least 50 vol %.

In one embodiment the delivery device further comprises: a further nosepiece for fitting to the other nostril of the subject; and a pressure regulator which is fluidly connected to the other nosepiece, such as to provide for control of a pressure regime within the nasal airway of the subject.

In a further aspect the present invention provides a delivery device for providing a substance and an uptake enhancing gas, which acts to increase the uptake of the substance, to the nasal airway of a subject, the delivery device comprising: a nosepiece for fitting to one nostril of the subject; a mouthpiece through which the subject in use exhales and which is fluidly connected to the nosepiece; a substance supply unit which is fluidly connected to the nosepiece and operative to supply substance; and a scrubber which is operative at least to reduce the concentration of at least one gas from an exhaled breath of the subject as delivered through the mouthpiece and provide a gas flow to the nosepiece which has an increased concentration of at least one other, uptake enhancing gas which acts to increase the uptake of substance as delivered by the substance supply unit.

In one embodiment the substance supply unit is configured to deliver an aerosol spray.

In one embodiment the aerosol spray comprises a liquid aerosol spray.

In another embodiment the aerosol spray comprises a powder aerosol spray.

In another embodiment the substance supply unit is configured to deliver a liquid jet.

In a further embodiment the substance supply unit is configured to deliver a powder jet.

In one embodiment the substance supply unit is a breath-actuated unit which is actuated in response to exhalation by the subject through the mouthpiece.

In one embodiment the substance supply unit is actuatable in response to generation of a predeterminable flow rate through the nosepiece.

In another embodiment the substance supply unit is actuatable in response to generation of a predeterminable pressure at the nosepiece.

In one embodiment the scrubber is operative to reduce the concentration of at least two gases from an exhaled breath of the subject.

In one embodiment the at least one gas comprises nitrogen.

In one embodiment the at least one gas comprises oxygen.

In one embodiment the at least one other, uptake enhancing gas comprises oxygen.

In one embodiment the at least one gas comprises carbon dioxide.

In one embodiment the at least one, other uptake enhancing gas comprises carbon dioxide.

Preferably, the scrubber is operative to provide a gas flow which has a concentration of the at least one other, uptake enhancing gas of at least 10 vol %.

More preferably, the scrubber is operative to provide a gas flow which has a concentration of the at least one, other uptake enhancing gas of at least 15 vol %.

Still more preferably, the scrubber is operative to provide a gas flow which has a concentration of the at least one, other uptake enhancing gas of at least 20 vol %.

Yet more preferably, the scrubber is operative to provide a gas flow which has a concentration of the at least one, other uptake enhancing gas of at least 30 vol %.

Still yet more preferably, the scrubber is operative to provide a gas flow which has a concentration of the at least one, other uptake enhancing gas of at least 40 vol %.

Yet still more preferably, the scrubber is operative to provide a gas flow which has a concentration of the at least one, other uptake enhancing gas of at least 50 vol %.

In one embodiment the delivery device further comprises: a further nosepiece for fitting to the other nostril of the subject; and a pressure regulator which is fluidly connected to the other nosepiece, such as to provide for control of a pressure regime within the nasal airway of the subject.

In a still further aspect the present invention provides a delivery device for providing a substance and an uptake enhancing gas, which acts to increase the uptake of the substance, to the nasal airway of a subject, the delivery device comprising: a nosepiece for fitting to one nostril of the subject; a substance supply unit which is fluidly connected to the nosepiece and operative to supply substance; and an uptake enhancing gas supply unit for supplying at least one uptake enhancing gas to the nosepiece, such as to provide for delivery of the at least one uptake enhancing gas to the nasal airway of the subject, which acts to increase the uptake of substance as delivered by the substance supply unit.

In one embodiment the substance supply unit is configured to deliver an aerosol spray.

In one embodiment the aerosol spray comprises a liquid aerosol spray.

In another embodiment the aerosol spray comprises a powder aerosol spray.

In another embodiment the substance supply unit is configured to deliver a liquid jet.

In a further embodiment the substance supply unit is configured to deliver a powder jet.

In one embodiment the at least one uptake enhancing gas comprises carbon dioxide.

In one embodiment the at least one uptake enhancing gas comprises nitric oxide.

In one embodiment the at least one uptake enhancing gas comprises oxygen.

In one embodiment the at least one uptake enhancing gas comprises helium.

In one embodiment the delivery device further comprises: a mouthpiece through which the subject in use exhales.

In one embodiment the mouthpiece is fluidly connected to the nosepiece, such that a gas flow as developed from an exhalation breath of the subject is delivered through the nosepiece.

In another embodiment the mouthpiece is fluidly separated from the nosepiece, such that a gas flow as developed from an exhalation breath of the subject is not delivered through the nosepiece.

In one embodiment the uptake enhancing gas supply unit comprises an uptake enhancing gas generator which is operative to generate at least one uptake enhancing gas.

In one embodiment the uptake enhancing gas generator is operative to generate at least one uptake enhancing gas on exhalation by the subject through the mouthpiece.

In one embodiment the uptake enhancing gas generator comprises an uptake enhancing gas generating agent which reacts to generate the at least one uptake enhancing gas.

In one embodiment the uptake enhancing gas generator comprises an uptake enhancing gas generating agent which is reactive to moisture in the exhalation breath of the subject.

In another embodiment the uptake enhancing gas supply unit comprises a gas supply which is actuatable to deliver at least one uptake enhancing gas.

In one embodiment the uptake enhancing gas supply unit comprises a breath-actuated release mechanism which actuates the gas supply to deliver at least one uptake enhancing gas in response to exhalation by the subject through the mouthpiece.

Preferably, the delivery device provides a gas flow which has a concentration of the at least one uptake enhancing gas of at least 10 vol %.

More preferably, the delivery device provides a gas flow which has a concentration of the at least one uptake enhancing gas of at least 15 vol %.

Still more preferably, the delivery device provides a gas flow which has a concentration of the at least one uptake enhancing gas of at least 20 vol %.

Yet more preferably, the delivery device provides a gas flow which has a concentration of the at least one uptake enhancing gas of at least 30 vol %.

Still yet more preferably, the delivery device provides a gas flow which has a concentration of the at least one uptake enhancing gas of at least 40 vol %.

Yet still more preferably, the delivery device provides a gas flow which has a concentration of the at least one uptake enhancing gas of at least 50 vol %.

In one embodiment the delivery device further comprises: a further nosepiece for fitting to the other nostril of the subject; and a pressure regulator which is fluidly connected to the other nosepiece, such as to provide for control of a pressure regime within the nasal airway of the subject.

In a yet further aspect the present invention provides a delivery device for providing a substance and an uptake enhancing gas, which acts to increase the uptake of the substance, to the nasal airway of a subject, the delivery device comprising: a nosepiece for fitting to one nostril of the subject; and a delivery unit which is fluidly connected to the nosepiece and operative to supply a substance and an uptake enhancing agent, such as to provide for delivery of the substance and the uptake enhancing agent to the nasal airway of the subject, which acts to increase the uptake of the substance as delivered by the substance supply unit.

In one embodiment the delivery unit is configured to deliver an aerosol spray.

In one embodiment the aerosol spray comprises a liquid aerosol spray.

In another embodiment the aerosol spray comprises a powder aerosol spray.

In another embodiment the delivery unit is configured to deliver a liquid jet.

In a further embodiment the delivery unit is configured to deliver a powder jet.

In one embodiment the uptake enhancing agent comprises at least one uptake enhancing gas.

In one embodiment the delivery unit is operative to supply the substance and the at least one uptake enhancing gas from a container, such as a capsule or blister.

In another embodiment the uptake enhancing agent comprises an uptake enhancing gas generating agent which is delivered together with the substance to the nasal airway and yields at least one uptake enhancing gas on exposure to moisture on surfaces of the nasal airway.

In one embodiment the delivery unit is operative to supply the substance and the at least one uptake enhancing gas generating agent from a container, such as a capsule or blister.

In a further embodiment the uptake enhancing agent comprises an uptake enhancing gas generating agent which is contained in the delivery device and yields at least one uptake enhancing gas on exposure to moisture in the exhalation breath of the subject.

In one embodiment the delivery unit is operative to supply the substance from a container which contains the uptake enhancing gas generating agent.

In one embodiment the at least one uptake enhancing gas comprises carbon dioxide.

In one embodiment the at least one uptake enhancing gas comprises nitric oxide.

In one embodiment the at least one uptake enhancing gas comprises oxygen.

In one embodiment the at least one uptake enhancing gas comprises helium.

In one embodiment the delivery device further comprises: a mouthpiece through which the subject in use exhales.

In one embodiment the mouthpiece is fluidly connected to the nosepiece, such that a gas flow as developed from an exhalation breath of the subject is delivered through the nosepiece.

In another embodiment the mouthpiece is fluidly separated from the nosepiece, such that a gas flow as developed from an exhalation breath of the subject is not delivered through the nosepiece.

Preferably, the delivery device provides a gas flow which has a concentration of the at least one uptake enhancing gas of at least 10 vol %.

More preferably, the delivery device provides a gas flow which has a concentration of the at least one uptake enhancing gas of at least 15 vol %.

Still more preferably, the delivery device provides a gas flow which has a concentration of the at least one uptake enhancing gas of at least 20 vol %.

Yet more preferably, the delivery device provides a gas flow which has a concentration of the at least one uptake enhancing gas of at least 30 vol %.

Still yet more preferably, the delivery device provides a gas flow which has a concentration of the at least one uptake enhancing gas of at least 40 vol %.

Yet still more preferably, the delivery device provides a gas flow which has a concentration of the at least one uptake enhancing gas of at least 50 vol %.

In one embodiment the delivery device further comprises: a further nosepiece for fitting to the other nostril of the subject; and a pressure regulator which is fluidly connected to the other nosepiece, such as to provide for control of a pressure regime within the nasal cavity of the subject.

In yet another aspect the present invention provides a method of providing a therapeutic gas to the nasal airway of a subject, comprising the steps of: fitting a nosepiece to one nostril of the subject; and the subject exhaling through a mouthpiece which is fluidly connected to the nosepiece and a scrubber which at least reduces the concentration of at least one gas from the exhaled breath of the subject and provides a gas flow to the nosepiece which has an increased concentration of at least one other, therapeutic gas which provides a therapeutic effect.

In one embodiment the scrubber reduces the concentration of at least two gases from the exhaled breath of the subject.

In one embodiment the at least one gas comprises nitrogen.

In one embodiment the at least one gas comprises oxygen.

In one embodiment the at least one other, therapeutic gas comprises oxygen.

In one embodiment the at least one gas comprises carbon dioxide.

In one embodiment the at least one other, therapeutic gas comprises carbon dioxide.

Preferably, the scrubber provides a gas flow which has a concentration of the at least one other, therapeutic gas of at least 10 vol %.

More preferably, the scrubber provides a gas flow which has a concentration of the at least one other, therapeutic gas of at least 15 vol %.

Still more preferably, the scrubber provides a gas flow which has a concentration of the at least one other, therapeutic gas of at least 20 vol %.

Yet more preferably, the scrubber provides a gas flow which has a concentration of the at least one other, therapeutic gas of at least 30 vol %.

Still yet more preferably, the scrubber provides a gas flow which has a concentration of the at least one other, therapeutic gas of at least 40 vol %.

Yet still more preferably, the scrubber provides a gas flow which has a concentration of the at least one other, therapeutic gas of at least 50 vol %.

In one embodiment the method further comprises the step of: fitting a further nosepiece to the other nostril of the subject and a pressure regulator to the other nosepiece, such as to control a pressure regime within the nasal airway of the subject.

In a still further aspect the present invention provides a method of providing a therapeutic gas to the nasal airway of a subject, comprising the steps of: fitting a nosepiece to one nostril of the subject; and supplying at least one therapeutic gas to the nosepiece, such as to provide for delivery of the at least one therapeutic gas to the nasal airway of the subject.

In one embodiment the at least one therapeutic gas comprises carbon dioxide.

In one embodiment the at least one therapeutic gas comprises nitric oxide.

In one embodiment the at least one therapeutic gas comprises oxygen.

In one embodiment the at least one therapeutic gas comprises helium.

In one embodiment the method further comprises the step of: the subject exhaling through a mouthpiece.

In one embodiment the mouthpiece is fluidly connected to the nosepiece, such that a gas flow as developed from the exhalation breath of the subject is delivered through the nosepiece.

In another embodiment the mouthpiece is fluidly separated from the nosepiece, such that a gas flow as developed from the exhalation breath of the subject is not delivered through the nosepiece.

In one embodiment the step of supplying at least one therapeutic gas comprises the step of: generating at least one therapeutic gas on exhalation by the subject through the mouthpiece.

In one embodiment the step of supplying at least one therapeutic gas comprises the step of: generating at least one therapeutic gas from a therapeutic gas generating agent which reacts to generate the at least one therapeutic gas.

In one embodiment the therapeutic gas generating agent is reactive to moisture in the exhalation breath of the subject.

In another embodiment the step of supplying at least one therapeutic gas comprises the step of: actuating a gas supply to supply at least one therapeutic gas.

In one embodiment the step of supplying at least one therapeutic gas comprises the step of: actuating a gas supply to supply at least one therapeutic gas in response to exhalation by the subject through the mouthpiece.

Preferably, the at least one therapeutic gas is supplied in a gas flow at a concentration of at least 10 vol %.

More preferably, the at least one therapeutic gas is supplied in a gas flow at a concentration of at least 15 vol %.

Still more preferably, the at least one therapeutic gas is supplied in a gas flow at a concentration of at least 20 vol %.

Yet more preferably, the at least one therapeutic gas is supplied in a gas flow at a concentration of at least 30 vol %.

Still yet more preferably, the at least one therapeutic gas is supplied in a gas flow at a concentration of at least 40 vol %.

Yet still more preferably, the at least one therapeutic gas is supplied in a gas flow at a concentration of at least 50 vol %.

In one embodiment the method further comprises the step of: fitting a further nosepiece to the other nostril of the subject and a pressure regulator to the other nosepiece, such as to control a pressure regime within the nasal airway of the subject.

In a yet further aspect the present invention provides a method of providing a substance and an uptake enhancing gas, which acts to increase the uptake of the substance, to the nasal airway of a subject, comprising the steps of: fitting a nosepiece to one nostril of the subject; supplying a substance to the nosepiece; and the subject exhaling through a mouthpiece which is fluidly connected to the nosepiece and a scrubber which at least reduces the concentration of at least one gas from the exhaled breath of the subject and provides a gas flow to the nosepiece which has an increased concentration of at least one other, uptake enhancing gas which acts to increase the uptake of substance.

In one embodiment the substance is delivered as an aerosol spray.

In one embodiment the aerosol spray comprises a liquid aerosol spray.

In another embodiment the aerosol spray comprises a powder aerosol spray.

In another embodiment the substance is delivered as a liquid jet.

In a further embodiment the substance is delivered as a powder jet.

In one embodiment the step of supplying substance comprises the step of:

supplying substance to the nosepiece in response to exhalation by the subject through the mouthpiece.

In one embodiment the substance is supplied in response to generation of a predeterminable flow rate through the nosepiece.

In another embodiment the substance is supplied in response to generation of a predeterminable pressure at the nosepiece.

In one embodiment the scrubber reduces the concentration of at least two gases from the exhaled breath of the subject.

In one embodiment the at least one gas comprises nitrogen.

In one embodiment the at least one gas comprises oxygen.

In one embodiment the at least one other, uptake enhancing gas comprises oxygen.

In one embodiment the at least one gas comprises carbon dioxide.

In one embodiment the at least one, other uptake enhancing gas comprises carbon dioxide.

Preferably, the scrubber provides a gas flow which has a concentration of the at least one other, uptake enhancing gas of at least 10 vol %.

More preferably, the scrubber provides a gas flow which has a concentration of the at least one, other uptake enhancing gas of at least 15 vol %.

Still more preferably, the scrubber provides a gas flow which has a concentration of the at least one, other uptake enhancing gas of at least 20 vol %.

Yet more preferably, the scrubber provides a gas flow which has a concentration of the at least one, other uptake enhancing gas of at least 30 vol %.

Still yet more preferably, the scrubber provides a gas flow which has a concentration of the at least one, other uptake enhancing gas of at least 40 vol %.

Yet still more preferably, the scrubber provides a gas flow which has a concentration of the at least one, other uptake enhancing gas of at least 50 vol %.

In one embodiment the method further comprises the step of: fitting a further nosepiece to the other nostril of the subject and a pressure regulator to the other nosepiece, such as to control a pressure regime within the nasal airway of the subject.

In still another aspect the present invention provides a method of providing a substance and an uptake enhancing gas, which acts to increase the uptake of the substance, to the nasal airway of a subject, comprising the steps of: fitting a nosepiece to one nostril of the subject; supplying a substance to the nosepiece, such as to provide for delivery of the substance to the nasal airway of the subject; and supplying at least one uptake enhancing gas to the nosepiece, such as to provide for delivery of the at least one uptake enhancing gas to the nasal airway of the subject, which acts to increase the uptake of substance.

In one embodiment the substance is delivered as an aerosol spray.

In one embodiment the aerosol spray comprises a liquid aerosol spray.

In another embodiment the aerosol spray comprises a powder aerosol spray.

In another embodiment the substance is delivered as a liquid jet.

In a further embodiment the substance is delivered as a powder jet.

In one embodiment the at least one uptake enhancing gas comprises carbon dioxide.

In one embodiment the at least one uptake enhancing gas comprises nitric oxide.

In one embodiment the at least one uptake enhancing gas comprises oxygen.

In one embodiment the at least one uptake enhancing gas comprises helium.

In one embodiment the method further comprises the step of: the subject exhaling through a mouthpiece.

In one embodiment the mouthpiece is fluidly connected to the nosepiece, such that a gas flow as developed from the exhalation breath of the subject is delivered through the nosepiece.

In another embodiment the mouthpiece is fluidly separated from the nosepiece, such that a gas flow as developed from the exhalation breath of the subject is not delivered through the nosepiece.

In one embodiment the step of supplying at least one uptake enhancing gas comprises the step of: generating at least one uptake enhancing gas on exhalation by the subject through the mouthpiece.

In one embodiment the step of supplying at least one uptake enhancing gas comprises the step of: generating at least one uptake enhancing gas from an uptake enhancing gas generating agent which reacts to generate the at least one uptake enhancing gas.

In one embodiment the uptake enhancing gas generating agent is reactive to moisture in the exhalation breath of the subject.

In another embodiment the step of supplying at least one uptake enhancing gas comprises the step of: actuating a gas supply to supply at least one uptake enhancing gas.

In one embodiment the step of supplying at least one uptake enhancing gas comprises the step of: actuating a gas supply to supply at least one uptake enhancing gas in response to exhalation by the subject through the mouthpiece.

Preferably, the at least one uptake enhancing gas is supplied in a gas flow at a concentration of at least 10 vol %.

More preferably, the at least one uptake enhancing gas is supplied in a gas flow at a concentration of at least 15 vol %.

Still more preferably, the at least one uptake enhancing gas is supplied in a gas flow at a concentration of at least 20 vol %.

Yet more preferably, the at least one uptake enhancing gas is supplied in a gas flow at a concentration of at least 30 vol %.

Still yet more preferably, the at least one uptake enhancing gas is supplied in a gas flow at a concentration of at least 40 vol %.

Yet still more preferably, the at least one uptake enhancing gas is supplied in a gas flow at a concentration of at least 50 vol %.

In one embodiment the method further comprises the step of: fitting a further nosepiece to the other nostril of the subject and a pressure regulator to the other nosepiece, such as to control a pressure regime within the nasal airway of the subject.

In still yet another aspect the present invention provides a method of providing a substance and an uptake enhancing gas, which acts to increase the uptake of the substance, to the nasal airway of a subject, comprising the steps of: fitting a nosepiece to one nostril of the subject; and supplying a substance and an uptake enhancing agent to the nosepiece, such as to provide for delivery of the substance and the uptake enhancing agent to the nasal airway of the subject, which acts to increase the uptake of the substance.

In one embodiment one or both of the substance and the uptake enhancing agent are delivered as an aerosol spray.

In one embodiment the aerosol spray comprises a liquid aerosol spray.

In one embodiment the aerosol spray comprises a powder aerosol spray.

In another embodiment one or both of the substance and the uptake enhancing agent are delivered as a liquid jet.

In a further embodiment one or both of the substance and the uptake enhancing agent are delivered as a powder jet.

In one embodiment the uptake enhancing agent comprises at least one uptake enhancing gas.

In one embodiment the substance and the at least one uptake enhancing gas are delivered from a container, such as a capsule or blister.

In another embodiment the uptake enhancing agent comprises an uptake enhancing gas generating agent which is delivered together with the substance to the nasal airway and yields at least one uptake enhancing gas on exposure to moisture on surfaces of the nasal airway.

In one embodiment the substance and the at least one uptake enhancing gas generating agent are delivered from a container, such as a capsule or blister.

In a further embodiment the uptake enhancing agent comprises an uptake enhancing gas generating agent which is contained upstream of the nosepiece and yields at least one uptake enhancing gas on exposure to moisture in the exhalation breath of the subject.

In one embodiment the substance is delivered from a container, such as a capsule or a blister, which contains the uptake enhancing gas generating agent.

In one embodiment the at least one uptake enhancing gas comprises carbon dioxide.

In one embodiment the at least one uptake enhancing gas comprises nitric oxide.

In one embodiment the at least one uptake enhancing gas comprises oxygen.

In one embodiment the at least one uptake enhancing gas comprises helium.

In one embodiment the method further comprises the step of: the subject exhaling through a mouthpiece.

In one embodiment the mouthpiece is fluidly connected to the nosepiece, such that a gas flow as developed from the exhalation breath of the subject is delivered through the nosepiece.

In another embodiment the mouthpiece is fluidly separated from the nosepiece, such that a gas flow as developed from the exhalation breath of the subject is not delivered through the nosepiece.

Preferably, the at least one uptake enhancing gas is supplied in a gas flow at a concentration of at least 10 vol %.

More preferably, the at least one uptake enhancing gas is supplied in a gas flow at a concentration of at least 15 vol %.

Still more preferably, the at least one uptake enhancing gas is supplied in a gas flow at a concentration of at least 20 vol %.

Yet more preferably, the at least one uptake enhancing gas is supplied in a gas flow at a concentration of at least 30 vol %.

Still yet more preferably, the at least one uptake enhancing gas is supplied in a gas flow at a concentration of at least 40 vol %.

Yet still more preferably, the at least one uptake enhancing gas is supplied in a gas flow at a concentration of at least 50 vol %.

In one embodiment the method further comprises the step of: fitting a further nosepiece to the other nostril of the subject and a pressure regulator to the other nosepiece, such as to control a pressure regime within the nasal airway of the subject.

In a still further aspect the present invention provides a delivery device for delivering a gas to the nasal airway of a subject, in particular a therapeutic gas or an uptake enhancing gas in combination with an active substance, either as a powder or liquid, for enhanced uptake of the active substance.

In still another aspect the present invention provides a method of delivering a gas to the nasal airway of a subject, in particular a therapeutic gas or an uptake enhancing gas in combination with an active substance, either as a powder or liquid, for enhanced uptake of the active substance.

BRIEF DESCRIPTION OF THE DRAWINGS

Preferred embodiments of the present invention will now be described hereinbelow by way of example only with reference to the accompanying drawings, in which.

DETAILED DESCRIPTION OF THE INVENTION

Figure 1:
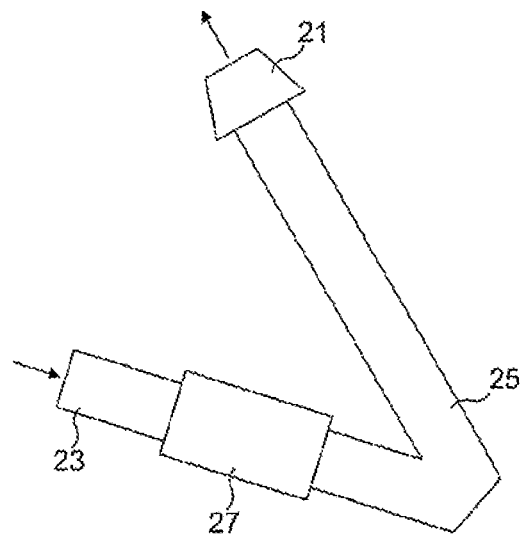
FIG. 1 illustrates a delivery device in accordance with a first embodiment of the present invention.

FIG. 1 illustrates a delivery device in accordance with a first embodiment of the present invention.

The delivery device comprises a nosepiece 21 for fitting in one nostril of a subject, in this embodiment to provide a fluid-tight seal therewith, a mouthpiece 23 through which the subject exhales, and a flow channel 25 fluidly connecting the nosepiece 21 and the mouthpiece 23.

The delivery device further comprises a scrubber 27 which is disposed in the flow channel 25 such as to remove one or more gases, in this embodiment one or both of oxygen and nitrogen, from the exhaled air and provide a gas flow which has an increased concentration of at least one gas, in this embodiment a concentration of carbon dioxide, which is increased to a concentration which provides a therapeutic effect.

Alveolar air typically has a composition of $N_2$—74.9 vol %, $O_2$—13.6 vol % and $CO_2$—5.3 vol %, which has a significantly increased concentration of carbon dioxide as compared to atmospheric air, which typically has the composition of $N_2$—78.62 vol % $O_2$—20.84 vol % and $CO_2$—0.04 vol %. Through use of the scrubber 27 to remove nitrogen and oxygen from the exhaled air, the concentration of carbon dioxide in the delivered gas flow can be increased significantly.

In one embodiment the scrubber 27 provides for a gas flow which has a concentration of therapeutic gas of at least 10 vol %, preferably at least 15 vol %, more preferably at least 20 vol %, still more preferably at least 30 vol %, yet more preferably at least 40 vol %, and yet still more preferably at least 50 vol %.

In one embodiment the scrubber 27 could be configured to provide a visual indication, such as by way of changing colour, to indicate when the efficiency of the scrubber 27 has reduced below a predetermined threshold.

With this configuration, a gas flow as developed by the exhalation breath of a subject is delivered through the nasal airway of the subject whilst the oropharyngeal velum of the subject is closed, thereby providing for the delivery of at least one therapeutic gas to the nasal airway and preventing inhalation of the at least one therapeutic gas.

Figure 2:
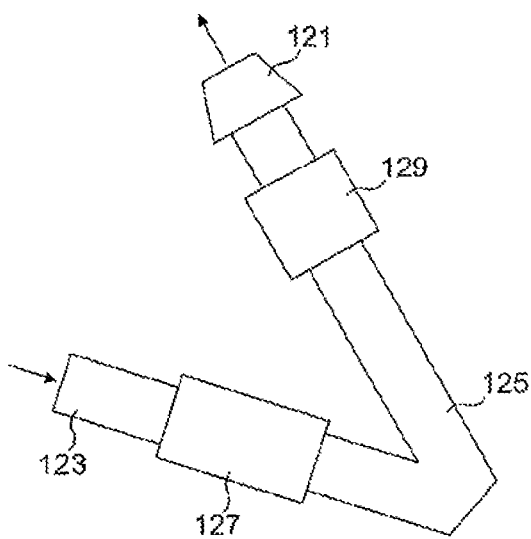
FIG. 2 illustrates a delivery device in accordance with a second embodiment of the present invention.

FIG. 2 illustrates a delivery device in accordance with a second embodiment of the present invention.

The delivery device comprises a nosepiece 121 for fitting in one nostril of a subject, in this embodiment to provide a fluid-tight seal therewith, a mouthpiece 123 through which the subject exhales, and a flow channel 125 fluidly connecting the nosepiece 121 and the mouthpiece 123.

The delivery device further comprises a scrubber 127 which is disposed in the flow channel 125 such as to remove one or more gases, in this embodiment one or both of oxygen and nitrogen, from the exhaled air and provide a gas flow which has an increased concentration of at least one gas, in this embodiment a concentration of carbon dioxide, which provides for enhanced uptake of a substance as delivered to the nasal airway, as will be described in more detail hereinbelow.

Alveolar air typically has a composition of $N_2$—74.9 vol %, $O_2$—13.6 vol % and $CO_2$—5.3 vol %, which has a significantly increased concentration of carbon dioxide as compared to atmospheric air, which typically has the composition of $N_2$—78.62 vol % $O_2$—20.84 vol % and $CO_2$—0.04 vol %. Through use of the scrubber 127 to remove nitrogen and oxygen from the exhaled air, the concentration of carbon dioxide in the delivered gas flow can be increased significantly.

In one embodiment the scrubber 127 provides for a gas flow which has a concentration of the uptake enhancing gas of at least 10 vol %, preferably at least 15 vol %, more preferably at least 20 vol %, still more preferably at least 30 vol %, yet more preferably at least 40 vol %, and yet still more preferably at least 50 vol %.

The delivery device further comprises a substance supply unit 129 for supplying metered doses of an active substance for delivery to the nasal airway of the subject.

In one embodiment the substance supply unit 129 is configured to deliver an aerosol spray, either as a liquid or a powder aerosol spray, but in an alternative embodiment could be configured to deliver a jet, that is, as a column of the substance, either as a liquid or powder jet.

In this embodiment the substance supply unit 129 comprises a mechanical delivery pump, in particular a liquid delivery pump or a powder delivery pump, which delivers metered doses of substance, on actuation thereof.

In another alternative embodiment the substance supply unit 129 could comprise a dry powder delivery unit which delivers metered doses of substance, as a dry powder, on actuation thereof. In one embodiment the substance supply unit 129 could provide for delivery of substance from a container, such as a capsule or blister.

In yet another alternative embodiment the substance supply unit 129 could comprise an aerosol canister which delivers metered volumes of a propellant, preferably a hydrofluoroalkane (HFA) propellant or the like, containing substance, either as a suspension or solution.

In this embodiment the substance supply unit 129 is a multi-dose unit for delivering a plurality of metered doses of the active substance. In another embodiment the substance supply unit 129 could be a single-dose unit for delivering a single metered dose of the active substance.

The substance supply unit 129 is pre-primeable, in this embodiment by loading a resilient element, and includes a breath-actuated release mechanism which, when triggered, releases the resilient element and actuates the substance supply unit 129 to deliver a metered dose of the active substance.

In this embodiment the trigger mechanism is configured to cause actuation of the substance supply unit 129 on generation of a predetermined flow rate through the flow channel 125.

In an alternative embodiment the trigger mechanism could be configured to cause actuation of the substance supply unit 129 on generation of a predetermined pressure in the flow channel 125.

With this configuration, a gas flow as developed by the exhalation breath of a subject is delivered through the nasal airway of the subject whilst the oropharyngeal velum of the subject is closed, with the velum being closed by the positive pressure as created in the oral cavity on exhalation, and a metered dose of an active substance is delivered into the nasal airway on generation of a predetermined flow rate through the nasal airway, or in an alternative embodiment a predetermined pressure in the nasal airway.

The gas flow as delivered through the nasal airway includes at least one uptake enhancing gas, in this embodiment carbon dioxide, which provides for enhanced uptake of the active substance, and inhalation of this gas is prevented by closure of the velum.

Figure 3:
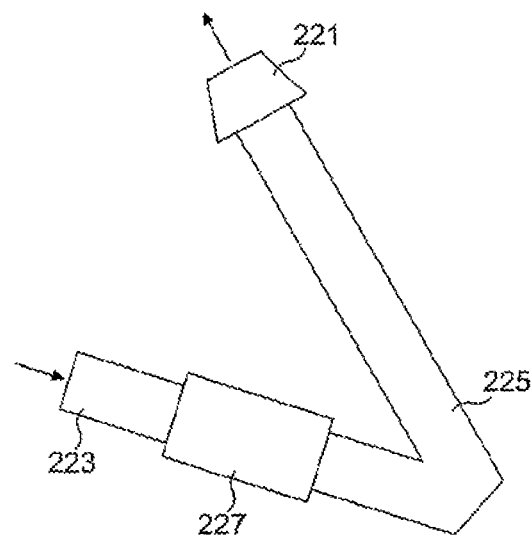
FIG. 3 illustrates a delivery device in accordance with a third embodiment of the present invention.

FIG. 3 illustrates a delivery device in accordance with a third embodiment of the present invention.

The delivery device comprises a nosepiece 221 for fitting in one nostril of a subject, in this embodiment to provide a fluid-tight seal therewith, a mouthpiece 223 through which the subject exhales, and a flow channel 225 fluidly connecting the nosepiece 221 and the mouthpiece 223.

The delivery device further comprises a gas generation unit 227 which is disposed in the flow channel 225 and provides for the generation of a therapeutic gas, in this embodiment carbon dioxide, which is entrained by the gas flow, as developed by the exhalation breath, into the nasal airway, and thereby provides a therapeutic effect on delivery into the nasal airway.

In this embodiment the gas generation unit 227 contains a powdered agent, here a mixture of a carbonate or bicarbonate salt, such as sodium bicarbonate, and an acid, such as citric acid, which, when exposed to moisture as contained in the exhaled breath, reacts to generate the therapeutic gas, here carbon dioxide. In addition to generating a therapeutic gas, the gas generation unit 227 has the particular benefit of acting as a moisture trap.

In this embodiment the powdered agent is contained in an air permeable member, typically a sachet, which can be replaced after one or more uses of the delivery device.

In this embodiment the gas generation unit 227 is disposed at an upstream end of the flow channel 225, such that substantially no condensation of moisture from the exhalation breath occurs prior to the exhalation breath being exposed to the gas generation unit 227.

In one embodiment the gas generation unit 227 provides a gas flow which has a concentration of the therapeutic gas of at least 10 vol %, preferably at least 15 vol %, more preferably at least 20 vol %, still more preferably at least 30 vol %, yet more preferably at least 40 vol %, and yet still more preferably at least 50 vol %.

With this configuration, a gas flow as developed by the exhalation breath of a subject is delivered through the nasal airway of the subject whilst the oropharyngeal velum of the subject is closed, thereby providing for the delivery of at least one therapeutic gas to the nasal airway and preventing inhalation of the at least one therapeutic gas.

Figure 4:
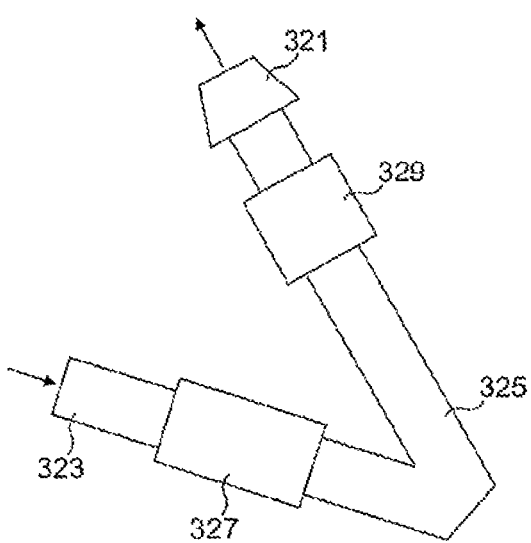
FIG. 4 illustrates a delivery device in accordance with a fourth embodiment of the present invention.

FIG. 4 illustrates a delivery device in accordance with a fourth embodiment of the present invention.

The delivery device comprises a nosepiece 321 for fitting in one nostril of a subject, in this embodiment to provide a fluid-tight seal therewith, a mouthpiece 323 through which the subject exhales, and a flow channel 325 fluidly connecting the nosepiece 321 and the mouthpiece 323.

The delivery device further comprises a gas generation unit 327 which is disposed in the flow channel 325 and provides for the generation of an uptake enhancing gas, in this embodiment carbon dioxide, which is entrained by the gas flow, as developed by the exhalation breath, into the nasal airway, and acts to enhance the uptake of an active substance as delivered to the nasal airway, as will be described in more detail hereinbelow.

In this embodiment the gas generation unit 327 contains a powdered agent, here a mixture of a carbonate or bicarbonate salt, such as sodium bicarbonate, and an acid, such as citric acid, which, when exposed to moisture as contained in the exhaled breath, reacts to generate the uptake enhancing gas, here carbon dioxide. In addition to generating an uptake enhancing gas, the gas generation unit 327 has the particular benefit of acting as a moisture trap, which reduces undesirable condensation within the remainder of the delivery device. Such condensation is particularly problematic in the delivery of powdered substances.

In this embodiment the powdered agent is contained in an air permeable member, typically a sachet, which can be replaced after one or more uses of the delivery device.

In this embodiment the gas generation unit 327 is disposed at an upstream end of the flow channel 325, such that substantially no condensation of moisture from the exhalation breath occurs prior to the exhalation breath being exposed to the gas generation unit 327.

In one embodiment the gas generation unit 327 provides a gas flow which has a concentration of the uptake enhancing gas of at least 10 vol %, preferably at least 15 vol %, more preferably at least 20 vol %, still more preferably at least 30 vol %, yet more preferably at least 40 vol %, and yet still more preferably at least 50 vol %.

The delivery device further comprises a substance supply unit 329 for supplying metered doses of an active substance for delivery to the nasal airway of the subject.

In one embodiment the substance supply unit 329 is configured to deliver an aerosol, either as a liquid or a powder aerosol, but in an alternative embodiment could be configured to deliver a jet, that is, as a column of the substance, either as a liquid or powder jet.

In this embodiment the substance supply unit 329 comprises a dry powder delivery unit which delivers metered doses of substance, as a dry powder, on actuation thereof. In one embodiment the substance supply unit 329 could provide for delivery of substance from a container, such as a capsule or blister.

In one alternative embodiment the substance supply unit 329 could comprise a mechanical delivery pump, in particular a liquid delivery pump or a powder delivery pump, which delivers metered doses of substance, on actuation thereof.

In yet another alternative embodiment the substance supply unit 329 could comprise an aerosol canister which delivers metered volumes of a propellant, preferably a hydrofluoroalkane (HFA) propellant or the like, containing substance, either as a suspension or solution.

In this embodiment the substance supply unit 329 is a multi-dose unit for delivering a plurality of metered doses of the active substance. In another embodiment the substance supply unit 329 could be a single-dose unit for delivering a single metered dose of the active substance.

The substance supply unit 329 is pre-primeable, in this embodiment by loading a resilient element, and includes a breath-actuated release mechanism which, when triggered, releases the resilient element and actuates the substance supply unit 329 to deliver a metered dose of the active substance.

In this embodiment the trigger mechanism is configured to cause actuation of the substance supply unit 329 on generation of a predetermined flow rate through the flow channel 325.

In an alternative embodiment the trigger mechanism could be configured to cause actuation of the substance supply unit 329 on generation of a predetermined pressure in the flow channel 325.

With this configuration, a gas flow as developed by the exhalation breath of a subject is delivered through the nasal airway of the subject whilst the oropharyngeal velum of the subject is closed, with the velum being closed by the positive pressure as created in the oral cavity on exhalation, and a metered dose of an active substance is delivered into the nasal airway on generation of a predetermined flow rate through the nasal airway, or in an alternative embodiment a predetermined pressure in the nasal airway. The gas flow as delivered through the nasal airway includes at least one uptake enhancing gas, in this carbon dioxide, which provides for enhanced uptake of the active substance, and inhalation of this gas is prevented by closure of the velum.

Figure 5:
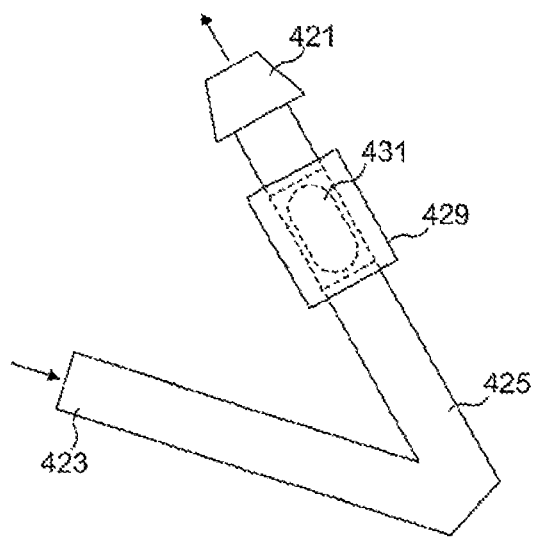
FIG. 5 illustrates a delivery device in accordance with a fifth embodiment of the present invention.

FIG. 5 illustrates a delivery device in accordance with a fifth embodiment of the present invention.

The delivery device comprises a nosepiece 421 for fitting in one nostril of a subject, in this embodiment to provide a fluid-tight seal therewith, a mouthpiece 423 through which the subject exhales, and a flow channel 425 fluidly connecting the nosepiece 421 and the mouthpiece 423.

The delivery device further comprises a delivery unit 429 for delivering metered doses of an active substance and an uptake enhancing agent for delivery to the nasal airway of the subject.

In this embodiment the uptake enhancing agent comprises a powdered substance, here a mixture of a carbonate or bicarbonate salt, such as sodium bicarbonate, and an acid, such as citric acid, which, when exposed to moisture at surfaces of the nasal mucosa, reacts to generate an uptake enhancing gas, here carbon dioxide, which provides for enhanced uptake of the active substance.

In one alternative embodiment the uptake enhancing agent could comprise an uptake enhancing gas, for example, carbon dioxide, which, when exposed to the nasal mucosa, provides for enhanced uptake of the active substance.

In another alternative embodiment the uptake enhancing agent could comprise an uptake enhancing gas, for example, carbon dioxide, which is generated from a powdered substance, for example, a mixture of a carbonate or bicarbonate salt, such as sodium bicarbonate, and an acid, such as citric acid, which, when exposed to moisture in the exhaled breath of the subject, reacts to generate the uptake enhancing gas, which provides for enhanced uptake of the active substance.

In this embodiment the delivery unit 429 is configured to deliver a powder aerosol, but in an alternative embodiment could be configured to deliver a powder jet, that is, as a powder column.

In this embodiment the substance supply unit 429 comprises a dry powder delivery unit which delivers a metered dose of an active substance and an uptake enhancing agent on actuation thereof.

In this embodiment the active substance and the uptake enhancing agent are dry powders, and the uptake enhancing agent reacts with moisture on the nasal mucosa to generate an uptake enhancing gas.

In the one alternative embodiment the active substance is a dry powder and the uptake enhancing agent is an accompanying gas.

In the other alternative embodiment the active substance is a dry powder and the uptake enhancing agent is a gas which is generated from the reaction of a powdered substance and moisture in the exhaled breath of the subject.

In this embodiment the substance supply unit 429 provides for delivery of the active substance and the uptake enhancing agent, both as dry powders, from a container 431, such as a capsule or blister, where a gas flow as developed from the exhalation breath of the subject acts to entrain the powder from the container 431 following opening, typically rupturing, of the same.

In the one alternative embodiment the substance supply unit 429 provides for delivery of the active substance, as a dry powder, and the uptake enhancing agent, as a gas, from a container 431, such as a capsule or blister, where the uptake enhancing agent is a gas which is released on opening, typically rupturing, the container 431, and a gas flow as developed from the exhalation breath of the subject acts to entrain the powdered active substance from the container 431 following opening of the same.

In the other alternative embodiment the substance supply unit 429 provides for delivery of the active substance, as a dry powder, and the uptake enhancing agent, as a gas, from a container 431, such as a capsule or blister, where the uptake enhancing gas is generated from a powdered substance contained within the container 431 on exposure to moisture in the exhaled breath of the subject following opening, typically rupturing, of the container 431, and a gas flow as developed from the exhalation breath of the subject acts to entrain the active substance from the container 431 following opening of the same.

In the described embodiments the delivery unit 429 could be a multi-dose unit for delivering a plurality of metered doses of the active substance and uptake enhancing agent, or a single-dose unit for delivering a single metered dose of the active substance and uptake enhancing agent.

In the configuration of this embodiment, a gas flow as developed from the exhalation breath of a subject is delivered through the nasal airway of the subject whilst the oropharyngeal velum of the subject is closed, with the velum being closed by the positive pressure as created in the oral cavity on exhalation, and a metered dose of an active substance and an uptake enhancing agent in combination is delivered into the nasal airway. In this embodiment the uptake enhancing agent reacts with moisture on contact with surfaces in the nasal cavity such as to generate an uptake enhancing gas thereat, here carbon dioxide, which provides for enhanced uptake of the active substance, and inhalation of this gas is prevented by closure of the velum.

In the configuration of the one alternative embodiment, a gas flow as developed from the exhalation breath of a subject is delivered through the nasal airway of the subject whilst the oropharyngeal velum of the subject is closed, with the velum being closed by the positive pressure as created in the oral cavity on exhalation, and a metered dose of an active substance and an uptake enhancing agent, as a gas, is delivered into the nasal airway. In this embodiment the uptake enhancing gas, here carbon dioxide, provides for enhanced uptake of the active substance, and inhalation of this gas is prevented by closure of the velum.

In the configuration of the other alternative embodiment, a gas flow as developed from the exhalation breath of a subject is delivered through the nasal airway of the subject whilst the oropharyngeal velum of the subject is closed, with the velum being closed by the positive pressure as created in the oral cavity on exhalation, and a metered dose of an active substance and an uptake enhancing agent, as a gas, for example, carbon dioxide, is delivered into the nasal airway. In this embodiment the uptake enhancing gas is generated by the reaction of a powdered substance, as contained within the container 431, with moisture from the exhalation breath of the subject, which provides for enhanced uptake of the active substance, and inhalation of this gas is prevented by closure of the velum.

Figure 6:
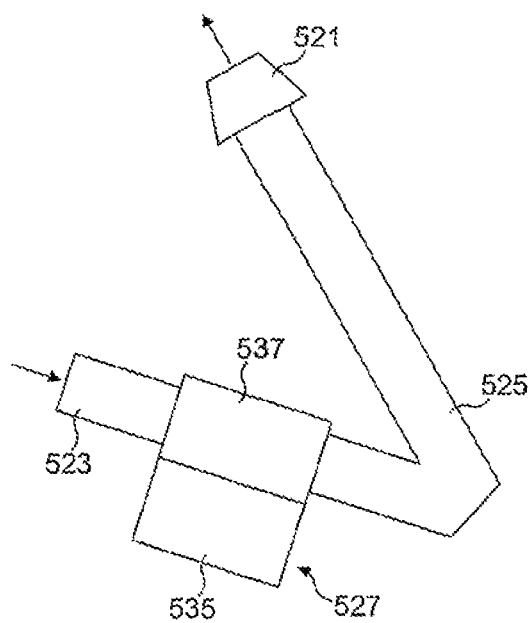
FIG. 6 illustrates a delivery device in accordance with a sixth embodiment of the present invention.

FIG. 6 illustrates a delivery device in accordance with a sixth embodiment of the present invention.

The delivery device comprises a nosepiece 521 for fitting in one nostril of a subject, in this embodiment to provide a fluid-tight seal therewith, a mouthpiece 523 through which the subject exhales, and a flow channel 525 fluidly connecting the nosepiece 521 and the mouthpiece 523.

The delivery device further comprises a gas supply unit 527 which is disposed in the flow channel 525 such as to deliver at least one therapeutic gas, in this embodiment carbon dioxide, to the gas flow as developed by the exhalation breath at such a concentration as to provide for a therapeutic effect.

In one embodiment the gas supply unit 527 provides for a gas flow which has a concentration of therapeutic gas of at least 10 vol %, preferably at least 15 vol %, more preferably at least 20 vol %, still more preferably at least 30 vol %, yet more preferably at least 40 vol %, and yet still more preferably at least 50 vol %.

In this embodiment the gas supply unit 527 includes a gas supply 535 and a breath-actuated release mechanism 537 which, when triggered, actuates the gas supply 535 to supply a therapeutic gas to the gas flow as developed through the flow channel 525. In one embodiment the gas supply 535 comprises a pressurized container which is vented to the flow channel 525 on triggering of the breath-actuated release mechanism 537.

In this embodiment the release mechanism 537 is configured to cause actuation of the gas supply unit 527 on generation of a predetermined flow rate through the flow channel 525.

In an alternative embodiment the release mechanism 537 could be configured to cause actuation of the gas supply unit 527 on generation of a predetermined pressure in the flow channel 525.

With this configuration, a gas flow as developed by the exhalation breath of a subject is delivered through the nasal airway of the subject whilst the oropharyngeal velum of the subject is closed, with the velum being closed by the positive pressure as created in the oral cavity on exhalation, and at least one therapeutic gas is delivered to the gas flow. The at least one therapeutic gas is thus entrained into the nasal airway and inhalation of the at least one therapeutic gas is prevented by closure of the velum.

Figure 7:
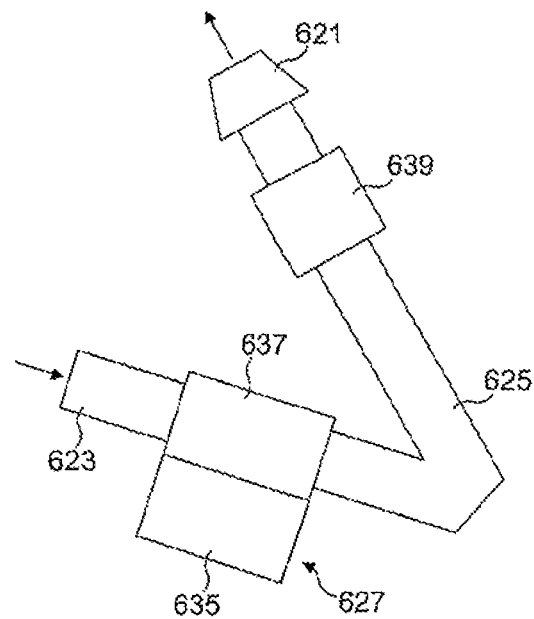
FIG. 7 illustrates a delivery device in accordance with a seventh embodiment of the present invention.

FIG. 7 illustrates a delivery device in accordance with a seventh embodiment of the present invention.

The delivery device comprises a nosepiece 621 for fitting in one nostril of a subject, in this embodiment to provide a fluid-tight seal therewith, a mouthpiece 623 through which the subject exhales, and a flow channel 625 fluidly connecting the nosepiece 621 and the mouthpiece 623.

The delivery device further comprises a gas supply unit 627 which is disposed in the flow channel 625 such as to deliver at least one uptake enhancing gas, in this embodiment carbon dioxide, to the gas flow as developed by the exhalation breath of the subject at such a concentration as to provide for enhanced uptake of an active substance as delivered to the nasal airway, as will be described in more detail hereinbelow.

In one embodiment the gas supply unit 627 provides for a gas flow which has a concentration of an uptake enhancing gas of at least 10 vol %, preferably at least 15 vol %, more preferably at least 20 vol %, still more preferably at least 30 vol %, yet more preferably at least 40 vol %, and yet still more preferably at least 50 vol %.

In this embodiment the gas supply unit 627 includes a gas supply 635 and a breath-actuated release mechanism 637 which, when triggered, actuates the gas supply 635 to supply an uptake enhancing gas to the gas flow as developed through the flow channel 625. In one embodiment the gas supply 635 comprises a pressurized container which is vented to the flow channel 625 on triggering of the breath-actuated release mechanism 637.

In this embodiment the release mechanism 637 is configured to cause actuation of the gas supply unit 627 on generation of a predetermined flow rate through the flow channel 625.

In an alternative embodiment the release mechanism 637 could be configured to cause actuation of the gas supply unit 627 on generation of a predetermined pressure in the flow channel 625.

The delivery device further comprises a substance supply unit 639 for supplying metered doses of an active substance for delivery to the nasal airway of the subject.

In one embodiment the substance supply unit 639 is configured to deliver an aerosol, either as a liquid or a powder aerosol, but in an alternative embodiment could be configured to deliver a jet, that is, as a column of the substance, either as a liquid or powder jet.

In this embodiment the substance supply unit 639 comprises a dry powder delivery unit which delivers metered doses of substance, as a dry powder, on actuation thereof. In one embodiment the substance supply unit 639 could provide for delivery of substance from a container, such as a capsule or blister.

In one alternative embodiment the substance supply unit 639 could comprise a mechanical delivery pump, in particular a liquid delivery pump or a powder delivery pump, which delivers metered doses of substance, on actuation thereof.

In yet another alternative embodiment the substance supply unit 639 could comprise an aerosol canister which delivers metered volumes of a propellant, preferably a hydrofluoroalkane (HFA) propellant or the like, containing substance, either as a suspension or solution.

In this embodiment the substance supply unit 639 is a multi-dose unit for delivering a plurality of metered doses of the active substance. In another embodiment the substance supply unit 639 could be a single-dose unit for delivering a single metered dose of the active substance.

The substance supply unit 639 is pre-primeable, in this embodiment by loading a resilient element, and includes a breath-actuated release mechanism which, when triggered, releases the resilient element and actuates the substance supply unit 639 to deliver a metered dose of the active substance.

In this embodiment the trigger mechanism is configured to cause actuation of the substance supply unit 639 on generation of a predetermined flow rate through the flow channel 625.

In an alternative embodiment the trigger mechanism could be configured to cause actuation of the substance supply unit 639 on generation of a predetermined pressure in the flow channel 625.

With this configuration, a gas flow as developed by the exhalation breath of a subject is delivered through the nasal airway of the subject whilst the oropharyngeal velum of the subject is closed, with the velum being closed by the positive pressure as created in the oral cavity on exhalation, and, on generation of a predetermined flow rate through the nasal airway, or in an alternative embodiment a predetermined pressure in the nasal airway, at least one uptake enhancing gas is delivered to the gas flow and a metered dose of an active substance is delivered into the nasal airway. The at least one uptake enhancing gas, in this embodiment carbon dioxide, provides for enhanced uptake of the active substance, and inhalation of this gas is prevented by closure of the velum.

Figure 8:
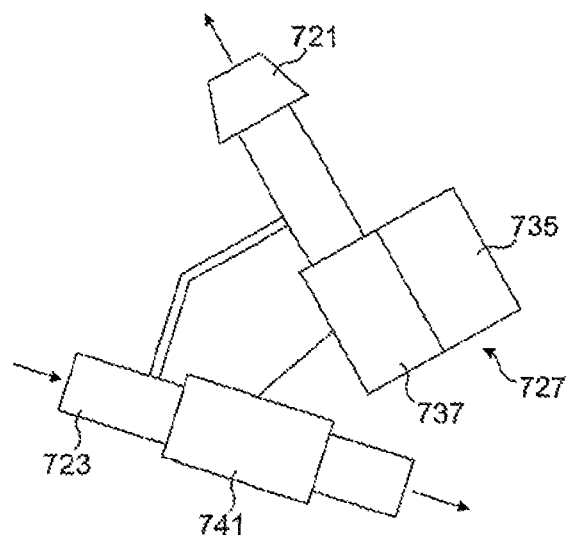
FIG. 8 illustrates a delivery device in accordance with an eighth embodiment of the present invention.

FIG. 8 illustrates a delivery device in accordance with an eighth embodiment of the present invention.

The delivery device comprises a nosepiece 721 for fitting in one nostril of a subject, in this embodiment to provide a fluid-tight seal therewith, and a mouthpiece 723 through which the subject exhales.

The delivery device further comprises a gas supply unit 727 which is fluidly connected to the nosepiece 721 such as to deliver at least one therapeutic gas, in this embodiment carbon dioxide, to the nasal airway at such a concentration as to provide for a therapeutic effect, as will be described in more detail hereinbelow.

In one embodiment the gas supply unit 727 provides for a gas flow which has a concentration of a therapeutic gas of at least 10 vol %, preferably at least 15 vol %, more preferably at least 20 vol %, still more preferably at least 30 vol %, yet more preferably at least 40 vol %, and yet still more preferably at least 50 vol %.

In this embodiment the gas supply unit 727 includes a gas supply 735 and a release mechanism 737 which, when triggered, actuates the gas supply 735 to deliver a therapeutic gas to the nosepiece 721 and into the nasal airway of the subject. In one embodiment the gas supply 735 comprises a pressurized container which is vented to the nosepiece 721 on triggering of the release mechanism 737.

The delivery device further comprises an exhalation sensor 741 which is fluidly connected to the mouthpiece 723 such as to detect exhalation through the mouthpiece 723 by the subject and operatively connected to the release mechanism 737 of the gas supply unit 727, such as to provide for triggering of the gas supply unit 727 in response to exhalation by the subject.

In this embodiment the exhalation sensor 741 is a flow sensor which is configured to cause actuation of the gas supply unit 727 on generation of a predetermined flow rate through the mouthpiece 723.

In an alternative embodiment the exhalation sensor 741 could be a pressure sensor which is configured to cause actuation of the gas supply unit 727 on generation of a predetermined pressure at the mouthpiece 723.

With this configuration, a gas flow containing at least one therapeutic gas is delivered through the nasal airway of the subject in response to exhalation by the subject whilst the oropharyngeal velum of the subject is closed, with the velum being closed by the positive pressure as created in the oral cavity on exhalation. In this way, at least one therapeutic gas is delivered to the nasal airway, and inhalation of the at least one therapeutic gas is prevented by closure of the velum.

Figure 9:
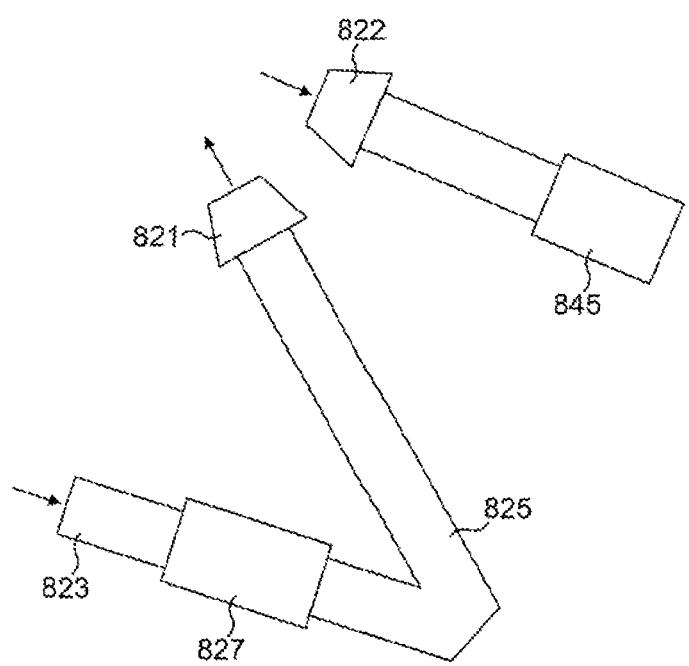
FIG. 9 illustrates a delivery device in accordance with a ninth embodiment of the present invention.

FIG. 9 illustrates a delivery device in accordance with a ninth embodiment of the present invention.

The delivery device comprises first and second nosepieces 821, 822 for fitting in the respective nostrils of a subject, in this embodiment to provide a fluid-tight seal therewith, a mouthpiece 823 through which the subject exhales, and a flow channel 825 which fluidly connects one nosepiece 821 and the mouthpiece 823.

The delivery device further comprises a scrubber 827 which is disposed in the flow channel 825 such as to remove one or more gases, in this embodiment one or both of oxygen and nitrogen, from the exhaled air and provide a gas flow which has an increased concentration of at least one gas, in this embodiment a concentration of carbon dioxide, which is increased to a concentration which provides a therapeutic effect.

Alveolar air typically has a composition of $N_2$—74.9 vol %, $O_2$—13.6 vol % and $CO_2$—5.3 vol %, which has a significantly increased concentration of carbon dioxide as compared to atmospheric air, which typically has the composition of $N_2$—78.62 vol % $O_2$—20.84 vol % and $CO_2$—0.04 vol %. Through use of the scrubber 827 to remove nitrogen and oxygen from the exhaled air, the concentration of carbon dioxide in the delivered gas flow can be increased significantly.

In one embodiment the scrubber 827 provides for a gas flow which has a concentration of therapeutic gas of at least 10 vol %, preferably at least 15 vol %, more preferably at least 20 vol %, still more preferably at least 30 vol %, yet more preferably at least 40 vol %, and yet still more preferably at least 50 vol %.

In one embodiment the scrubber 827 could be configured to provide a visual indication, such as by way of changing colour, to indicate when the efficiency of the scrubber 827 has reduced below a predetermined threshold.

The delivery device further comprises a pressure regulator 845 which is fluidly connected to the other nosepiece 822 such as provide for a predetermined pressure regime in the nasal airway. In one embodiment providing an increased pressure in the nasal airway acts to open ostia in the treatment of nasal conditions, such as sinus ostia in the treatment of sinusitis.

In this embodiment the pressure regulator 845 comprises a progressive flow resistor which provides a progressively increasing resistance to the exhaled air from the exhalation breath of a subject. In one embodiment the progressive flow resistor comprises an inflatable balloon which is manipulatable by the user to allow for control the pressure within the nasal cavity.

In another embodiment the pressure regulator 845 could be configured to provide a predetermined flow resistance to the exhaled air flow.

In a further embodiment the pressure regulator 845 could be configured to maintain a predetermined pressure regime in the nasal airway.

In one embodiment the pressure regulator 845 could be configured to maintain a fixed pressure in the nasal airway, where as one of either of a negative or positive pressure, in one embodiment through the use of an auxiliary pump.

In an alternative embodiment the pressure regulator 845 could be configured to generate an alternating pressure within the nasal airway of a subject. By cycling the pressure within the nasal airway, improved delivery of therapeutic gas to the paranasal sinuses, the tuba auditiva and the middle ears can be achieved.

In a further embodiment the delivery device could include a vibration generator for generating vibrations in structures of the nasal airway of the subject, such as by the provision of sound waves of a predeterminable frequency, which act to improve communication through the ostia, in particular in ventilating the sinuses.

With this configuration, a gas flow as developed by the exhalation breath of a subject is delivered through the nasal airway of the subject whilst the oropharyngeal velum of the subject is closed, thereby providing for the delivery of at least one therapeutic gas to the nasal airway and preventing inhalation of the at least one therapeutic gas.

Finally, it will be understood that the present invention has been described in its preferred embodiments and can be modified in many different ways without departing from the scope of the invention as defined by the appended claims.

For example, in one modification, the first to eighth embodiments could be modified in the manner of the ninth embodiment to include a second, outlet nosepiece and an associated pressure regulator.

Also, embodiments have been described specifically in relation to the generation of carbon dioxide as either a therapeutic or uptake enhancing gas. In other embodiments, which utilize nitric oxide as either the therapeutic or uptake enhancing gas, the nitric oxide can be generated from a mixture of sodium nitroprusside and an acid, such as citric acid, which, when exposed to moisture, as, for example, contained in the exhaled breath, reacts to generate the therapeutic gas. Also, in such reactions, GRAS excipients can be utilized to control the rate of gas generation.

Further, in one alternative embodiment, in order to alter the relative concentrations of carbon dioxide, nitrogen and oxygen in the exhaled breath of a subject, the exhaled breath could be passed through a liquid which is saturated with carbon dioxide, has substantially the same partial pressure of oxygen as the exhaled breath and a reduced partial pressure or absence of nitrogen, which results in the carbon dioxide equilibrating into the gas phase, the nitrogen equilibrating into the liquid and the oxygen concentration remaining substantially unchanged.

We claim:

1. A pharmaceutical delivery device for delivering a substance and a gas to a nasal airway of a subject, comprising:
    a nosepiece configured to fit to one nostril of the subject in use;
    a mouthpiece fluidly connected to the nosepiece and configured to fit to an oral cavity of the subject in use, through which the subject in use exhales creating a flow of exhalation breath;
    a substance supply unit fluidly connected to the nosepiece and configured to provide the substance into the flow of exhalation breath for delivery to the nasal airway of the subject; and
    a gas generation unit fluidly connected to the nosepiece and configured to provide the gas into the flow of exhalation breath for delivery to the nasal airway of the subject, wherein the gas generation unit includes an air-permeable container, containing a powder.

2. The delivery device of claim 1, wherein the powder, when exposed to the flow of exhalation breath, reacts to generate the gas.

3. The delivery device of claim 2, wherein the powder is configured to react to moisture in the flow of exhalation breath.

4. The delivery device of claim 2, wherein the powder includes a mixture of a carbonate or a bicarbonate salt and an acid.

5. The delivery device of claim 4, wherein the powder includes a mixture of sodium bicarbonate and an acid.

6. The delivery device of claim 4, wherein the acid is citric acid.

7. The delivery device of claim 4, wherein the powder includes a mixture of sodium bicarbonate and citric acid.

8. The delivery device of claim 2, wherein the gas is carbon dioxide.

9. The delivery device of claim 1, wherein the gas is carbon dioxide.

10. The delivery device of claim 1, wherein the container is replaceable.

11. The delivery device of claim 1, wherein the container is a sachet.

12. The delivery device of claim 1, wherein exhalation by the subject causes closure of an oropharyngeal velum of the subject.

13. The delivery device of claim 12, wherein closure of the oropharyngeal velum prevents inhalation of the gas by the subject.

14. The delivery device of claim 1, wherein the substance supply unit is configured to deliver an aerosol spray.

15. The delivery device of claim 1, wherein the substance is a powder.

16. The delivery device of claim 1, wherein the substance is a liquid.

17. A pharmaceutical delivery device for delivering a substance to a nasal airway of a subject, comprising:
    a nosepiece configured to fit to one nostril of the subject in use;
    a mouthpiece fluidly connected to the nosepiece and configured to fit to an oral cavity of the subject in use, through which the subject in use exhales creating a flow of exhalation breath;
    a substance supply unit fluidly connected to the nosepiece and configured to provide the substance into the flow of exhalation breath for delivery to the nasal airway of the subject; and
    a gas generation unit fluidly connected to the nosepiece and configured to generate carbon dioxide gas and provide the carbon dioxide gas into the flow of exhalation breath for delivery to the nasal airway of the subject, the gas generation unit including an air-permeable container, which contains a powder configured to react with, to the flow of exhalation breath to generate the carbon dioxide gas.

18. The delivery device of claim 17, wherein the substance is a powder.

19. The delivery device of claim 17, wherein the substance is a liquid.

20. The delivery device of claim 17, wherein the powder is configured to react to moisture in the flow of exhalation breath.

21. The delivery device of claim 17, wherein the powder includes a mixture of sodium bicarbonate and citric acid.

22. A pharmaceutical delivery device for delivering a substance and a gas to a nasal airway of a subject, comprising:
- a nosepiece configured to fit to one nostril of the subject in use;
- a mouthpiece fluidly connected to the nosepiece and configured to fit to an oral cavity of the subject in use, through which the subject in use exhales creating a flow of exhalation breath;
- a substance supply unit fluidly connected to the nosepiece and configured to provide the substance into the flow of exhalation breath for delivery to the nasal airway of the subject; and
- a gas generation unit fluidly connected to the nosepiece and configured to provide the gas into the flow of exhalation breath for delivery to the nasal airway of the subject, wherein the gas generation unit includes an air-permeable container.

* * * * *

UNITED STATES PATENT AND TRADEMARK OFFICE
CERTIFICATE OF CORRECTION

PATENT NO. : 11,690,969 B2
APPLICATION NO. : 16/986692
DATED : July 4, 2023
INVENTOR(S) : Per Gisle Djupesland et al.

Page 1 of 1

It is certified that error appears in the above-identified patent and that said Letters Patent is hereby corrected as shown below:

In the Claims

Claim 17, Column 24, Line 64, "to react with, to the flow of" should read --to react with the flow of--.

Signed and Sealed this
Fifth Day of September, 2023

Katherine Kelly Vidal
*Director of the United States Patent and Trademark Office*